US010869904B2

(12) United States Patent
Yoon et al.

(10) Patent No.: US 10,869,904 B2
(45) Date of Patent: *Dec. 22, 2020

(54) **PHARMACEUTICAL COMPOSITION FOR PREVENTING OR TREATING RESPIRATORY DISEASE COMPRISING EXTRACT OF *JUSTICIA PROCUMBENS* L**

(71) Applicant: DONG WHA PHARM. CO., LTD., Seoul (KR)

(72) Inventors: Joo Byoung Yoon, Hwaseong-si (KR); Hyun Yong Lee, Yongin-si (KR); Ji Hyun Youm, Suwon-si (KR); Kwang Hyun Kim, Yongin-si (KR); Ji Hyun Jeon, Hwaseong-si (KR); Hwan Bong Chang, Yongin-si (KR); Ji Young Woo, Hwaseong-Si (KR); Mi Hee Yoon, Yeonsu-gu (KR); Min Soo Choi, Suwon-si (KR); Dong Rack Choi, Seongnam-si (KR)

(73) Assignee: DONG WHA PHARM. CO., LTD., Seoul (KR)

( * ) Notice: Subject to any disclaimer, the term of this patent is extended or adjusted under 35 U.S.C. 154(b) by 102 days.

This patent is subject to a terminal disclaimer.

(21) Appl. No.: 16/093,829

(22) PCT Filed: Apr. 13, 2017

(86) PCT No.: PCT/KR2017/004033
§ 371 (c)(1),
(2) Date: Oct. 15, 2018

(87) PCT Pub. No.: WO2017/179931
PCT Pub. Date: Oct. 19, 2017

(65) Prior Publication Data
US 2019/0134126 A1 May 9, 2019

(30) Foreign Application Priority Data
Apr. 15, 2016 (KR) .................. 10-2016-0046123

(51) Int. Cl.
| | |
|---|---|
| *A61K 36/19* | (2006.01) |
| *A61K 31/36* | (2006.01) |
| *A23L 33/105* | (2016.01) |
| *A23L 33/10* | (2016.01) |
| *A61K 31/343* | (2006.01) |
| *A61P 11/00* | (2006.01) |
| *A61K 9/00* | (2006.01) |

(52) U.S. Cl.
CPC .............. *A61K 36/19* (2013.01); *A23L 33/10* (2016.08); *A23L 33/105* (2016.08); *A61K 9/0053* (2013.01); *A61K 31/343* (2013.01); *A61K 31/36* (2013.01); *A61P 11/00* (2018.01); *A23V 2002/00* (2013.01); *A23V 2200/314* (2013.01); *A23V 2250/082* (2013.01)

(58) Field of Classification Search
None
See application file for complete search history.

(56) References Cited

U.S. PATENT DOCUMENTS

2017/0360862 A1   12/2017   Yoon et al.

FOREIGN PATENT DOCUMENTS

| IN | 1330/MUM/2005 | 11/2005 |
| JP | 2007/230977 A | 9/2007 |
| KR | 2016-0044807 A | 4/2016 |

OTHER PUBLICATIONS

U.S. Appl. No. 15/519,116, filed Apr. 2017, Yoon; Joo Byoung.*
Office Action issued in corresponding Russian Application No. 2017116794/15(029034) dated Oct. 5, 2018, and English translation thereof (20 pages).
Chaukhamba Orientalia, Varanasi, and.8th, 1998 [time of origin 5th century], Indian database TKDL, document RS23/1486: http://www.tkdl.res.in/tkdl/LangDefault/Formulation/Member_Docs/BC/ <https://protect-us.mimecast.com/s/Jrk5Czp9YZuE31Xf4t2Mq?domain=tkdl.res.in> ayurveda/highlight.asp?a=/tkdl/LangDefault/Formulation/Member_Docs/ BC/Ayurveda/RS23-1486.asp&b=justicia+and+allergic?str=Global (2 pages).
Chaukhamba Sanskrit Sansthan, Varanasi, and.14th, 2001 [this book contains back references from 1000 B.C. to 18th century], Indian database TKDL, document AK/3011: http://www.tkdl.res.in/tkdl/LangDefault/Formulation/Member_Docs/BC/ <https://protect-us.mimecast.com/s/Jrk5Czp9YZuE31Xf4t2Mq?domain=tkdl.res.in> ayurveda/highlight.asp?a=/tkdl/LangDefault/Formulation/Member_Docs/ BC/Ayurveda/AK3011.asp&b=justicia+and+allergic?str=Global (5 pages).
Office Action issued in corresponding Japanese Application No. 2018-553180, dated Sep. 24, 2019 (4 pages).
Ueng, Yune-Fang et al. Inhibition of Benzo(a)pyrene Hydroxylation by Lignans Isolated from Justicia procumbens. Journal of Food and Drug Analysis, vol. 8, No. 4, 2000, pp. 309-314 (6 pages).

(Continued)

*Primary Examiner* — Michael Barker
(74) *Attorney, Agent, or Firm* — Osha Bergman Watanabe & Burton LLP

(57) ABSTRACT

The present invention relates to a pharmaceutical composition for preventing or treating respiratory disease, which comprises an alcohol or organic solvent extract of *Justicia procumbens* L. as an active ingredient, and to a pharmaceutical composition for preventing or treating respiratory disease, which comprises an alcohol or organic solvent extract of *Justicia procumbens* L., the extract comprising any one or more of justicidin A, justicidin B, justicidin C and phyllamyricin C, and also to a food composition for preventing or treating respiratory disease, which comprises the alcohol or organic solvent extract. The composition comprising the *Justicia procumbens* L. extract according to the present invention may inhibit abnormal overproliferation of splenocytes, may inhibit the secretion of allergic inflammatory cytokines, and exhibits an expectorant effect and an airway constriction inhibitory effect. Thus, it may effectively prevent, treat or improve respiratory disease.

27 Claims, 4 Drawing Sheets

(56) References Cited

OTHER PUBLICATIONS

Tsao, Lo-Ti et al. Justicidin A Inhibits the Transport of Tumor Necrosis Factor-a to Cell Surface in Lipopolysaccharide-Stimulated RAW 264.7 Macrophages. Molecular Pharmacology, vol. 65, No. 5, 2004, pp. 1063-1069 (7 pages).
Notice of Grant in corresponding Korean Application No. 10-2018-0110017, dated Jul. 18, 2019 (6 pages).
Park, Gil Byeong and Yang Chun Park. Effects of Mahaenggamseok-tang-gagambang on Immune Cells and Cytokines in OVA-Induced Asthmatic Mice. Korean Journal of Oriental Physiology & Pathology, 2009, vol. 23, No. 3, pp. 590-598—with partial translation (11 pages).
Database WPI, Week 201606, Thomson Scientific, London, GB; AN 2015-56965B & CN 104 800 718 A (Wang, Q) Jul. 29, 2015 (2 pages).
Extended European Search Report issued in corresponding European Patent Application No. 17782686.4, dated Nov. 13, 2019 (9 pages).
Pelaia, G., et. al., "Cellular Mechanisms Underlying Eosinophilic and Neutrophilic Airway Inflammation in Asthma", Mediators of inflammation, 2015 (9 pages).
Wilson, C. N., "Adenosine receptors and asthma in humans", British journal of pharmacology, 155(4), 475-486, 2008 (12 pages).
Correa, G. M. et al., "Chemical Constituents and Biological Activities of Species of Justicia—a Review", Revista Brasileira de Farmacognosia Brazilian, Journal of Pharmacognosy, vol. 22, No. 1, 2012, pp. 220-238 (19 pages).
Dogra, K. S. et al., "Assessment of Indian Medicinal Plants for the Treatment of Asthma", Journal of Medicinal Plants Research, vol. 9, No. 32, 2015, pp. 851-862 (12 pages).
Zhou, P. et al., "Preparative Isolation and Purification of Lignans from Justicia Procumbens Using High-speed countercurrent Chromatography in Stepwise Elution Mode", Molecules, vol. 20, 2015, pp. 7048-7058 (11 pages).
Velpandian, V. et al., "Clinical Evaluation of *Justicia tranquebariensis* L. in the Management of Bronchial Asthma", American Journal of Phytomedicine and Clinical Therapeutics, vol. 9, No. 2, 2014, pp. 1103-1111 (9 pages).
Savithramma, N. et al., "Ethnobotanical survey of plants used to treat asthma in Andhra Pradesh, India", Journal of Ethnopharmacology, vol. 113, pp. 54-61 (2007) (8 pages).
Rao, Y.K. et al., "Anti-inflammatory activities of constituents isolated from Phyllanthus polyphyllus" Journal of ethnopharmacology, 2006, 103(2), pp. 181-186 (6 pages).
English translation of International Search Report and Written Opinion issued in corresponding International Application No. PCT/KR2017/004033 dated Jul. 10, 2017 (14 pages).
Office Action with English translation issued in corresponding Japanese Application No. 2018-553180, dated Jan. 27, 2020 (6 pages).
Office Action issued in corresponding Australian Application No. 2017251303, dated Aug. 8, 2019 (3 pages).

\* cited by examiner

[Figure 1]
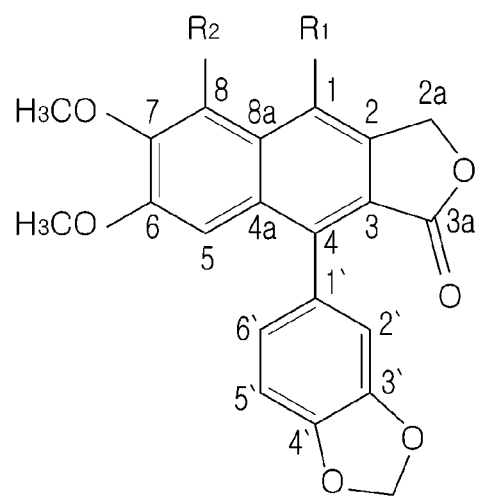
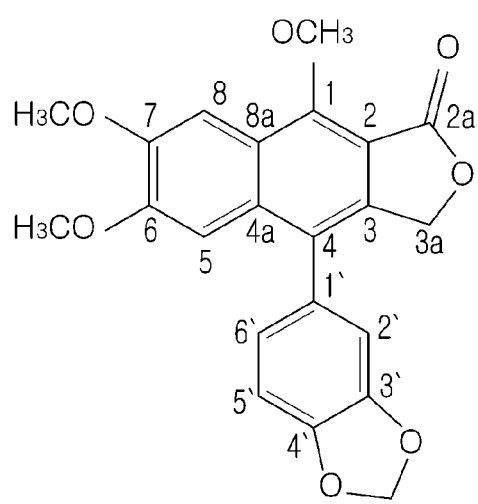
1 R₁ = R₂ = –H
2 R₁ = –OCH₃, R₂ = –H
4 R₁ = –H, R₂ = –OCH₃
3

[Figure 2]
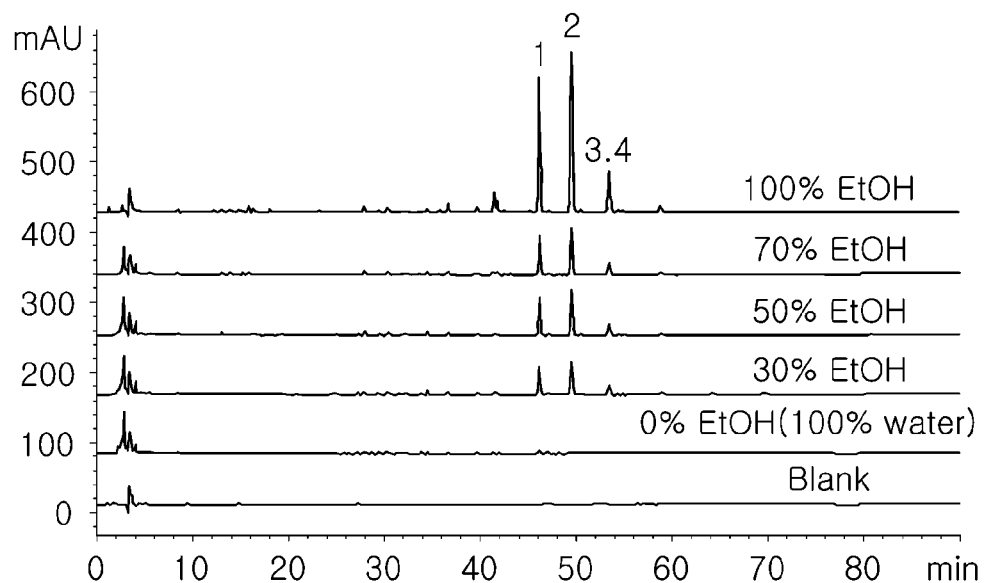
[Figure 3]
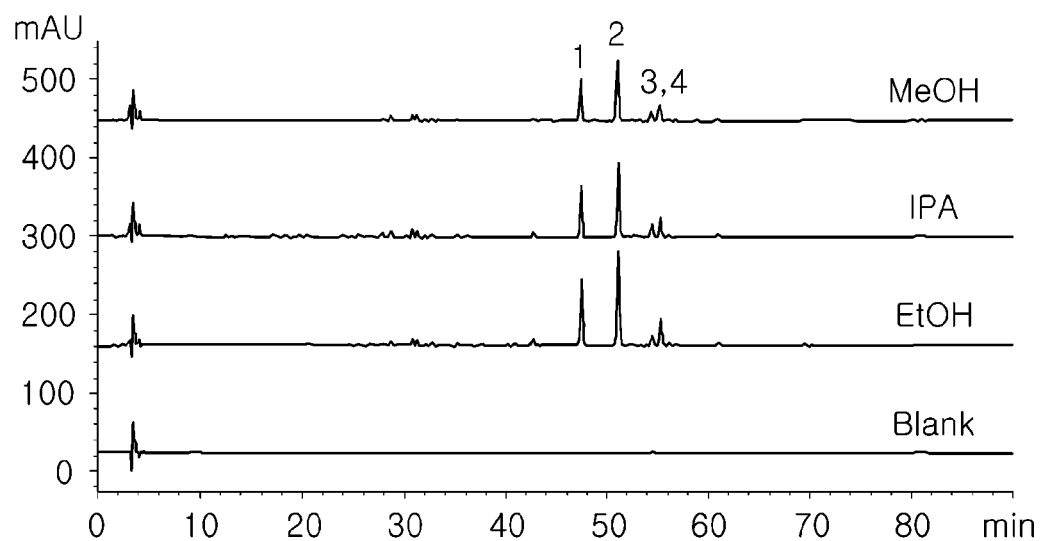

【Figure 4】
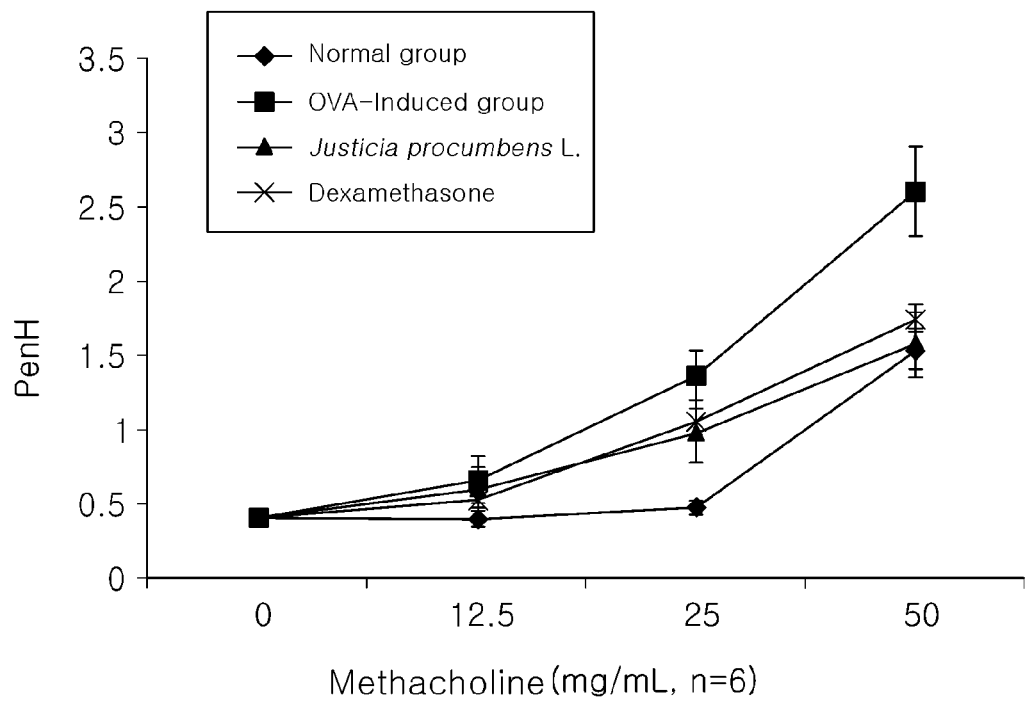
【Figure 5】
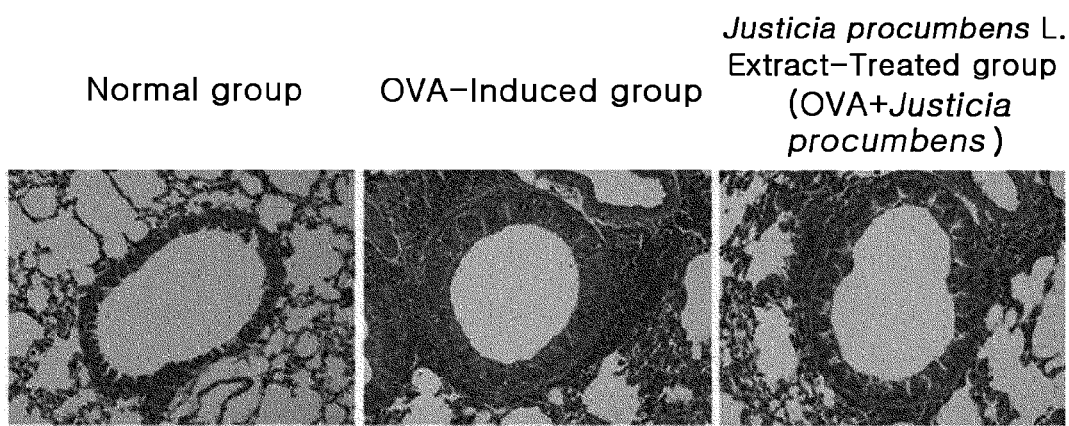

[Figure 6]
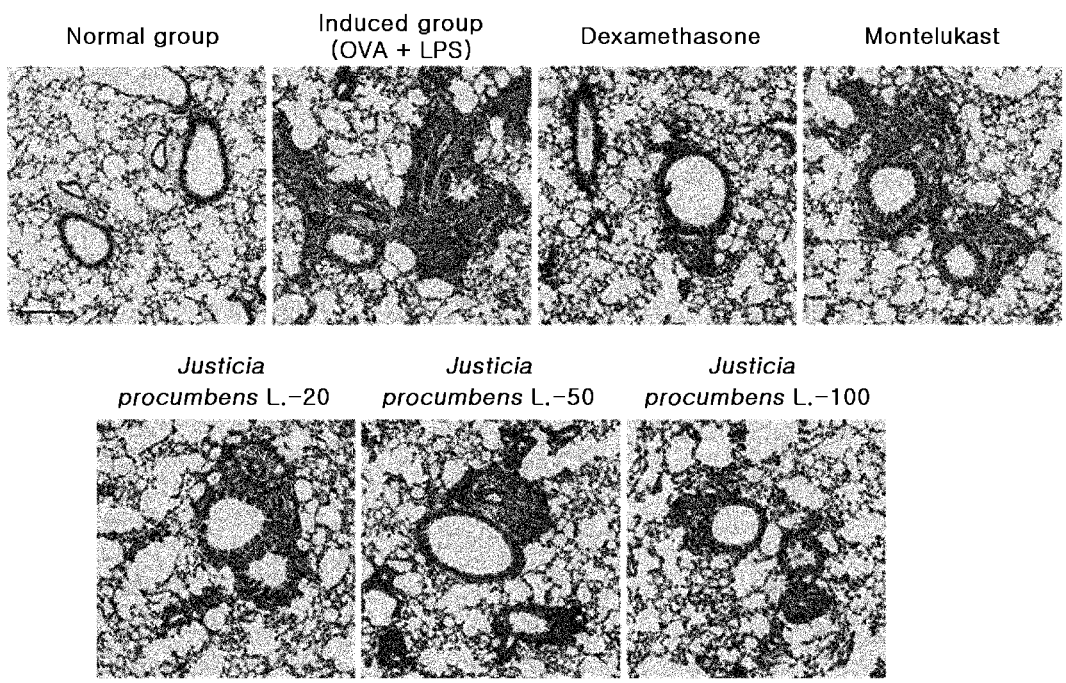

PHARMACEUTICAL COMPOSITION FOR PREVENTING OR TREATING RESPIRATORY DISEASE COMPRISING EXTRACT OF *JUSTICIA PROCUMBENS* L

TECHNICAL FIELD

The present invention relates to a pharmaceutical composition for preventing or treating respiratory disease, which comprises an alcohol or organic solvent extract of *Justicia procumbens* L., and to a food composition for preventing or improving respiratory disease, which comprises the extract as an active ingredient.

BACKGROUND ART

The respiratory system consists of the lungs, airways and respiratory muscles. The airways provide a pathway from the nasal or oral cavity from the lungs, and consist of the upper airway extending from the nasal or oral cavity to the pharynx, and the lower airway including the larynx, trachea and bronchus. Respiratory diseases refer to diseases associated mainly with the lungs and airways, and include, for example, cold, pneumonia, bronchitis, asthma, rhinitis, chronic obstructive pulmonary disease (COPD), and the like.

Asthma, a representative respiratory disease, is a disease having pathological features, including inflammation in the bronchi in the lungs, and airway narrowing, and shows symptoms, including difficulty breathing, coughing, wheezing, and the like. Asthma is classified according to its cause into allergic asthma caused by allergen-induced immune hypersensitivity, aspirin asthma caused by a particular drug, exercise-induced asthma caused by exercise, and heterogeneous diseases caused by various factors, including asthma with bacterial and viral infections, obesity or the like. It is known that inflammation in allergic asthma is allergic inflammation caused mainly by excessive activation of T helper (Th2) cells, unlike common inflammation, and that interleukine-4 and -5 (IL-4 and IL-5) derived from T helper 2 cells, immunoglobulin E (IgE), eosinophils, histamine, and the like are involved in allergic inflammation. Non-allergic asthma and some severe asthma symptoms are characterized by increased neutrophils compared with eosinophils, and characterized by increases in Th17 cells, iinterleukine-8, interferon-γ (IFN-γ) and the like (Pelaia, G., et. al., *Mediators of inflammation*, 2015, 2015).

Representative reasons why the airway narrows include blocking of the airway by mucus excessively secreted from the bronchial mucosa stimulated by inflammation, swelling of the bronchial mucosa, narrowing of the airway due to contraction of smooth muscles, and the like.

Meanwhile, chronic obstructive pulmonary disease (COPD), another respiratory disease, is a disease in which inflammatory reactions in the lungs occur mainly due to the inhalation of harmful particles or gases, like smoking, and for this reason, the airways are irreversibly obstructed, and thus the lung function is slowly deteriorated. Emphysema and chronic bronchitis are collectively referred to as chronic obstructive pulmonary disease. It shows symptoms, including difficulty breathing, coughing, sputum, and the like, similar to asthma. However, asthma is caused by temporary airway obstruction and can be reversibly recovered, whereas chronic obstructive pulmonary disease is characterized in that the lung function is not reversibly recovered.

Drugs for treating the above-described respiratory diseases can be classified mainly into controllers having anti-inflammatory activity, and relievers having bronchodilation activity. Glucocorticoid steroid drugs that are representative controllers have excellent anti-inflammatory effects, but cause serious side effects, such as growth retardation or osteoporosis, and for this reason, the use of inhalation drugs that locally act has been limited. Meanwhile, beta2-agonists that are representative relievers have excellent bronchodilation effects, but there are reported that they have no anti-inflammatory effect, and thus when these drugs are administered alone, asthma rather worsens. In addition, these drugs are also inhalation drugs. Inhalation drugs have the advantage of showing fast efficacy, but several reports have pointed out inconvenient administration of these drugs and, in particular, poor compliance with these drugs among more than half of the elderly and child patients. Representative oral drugs with high compliance include leukotriene receptor antagonists, and relievers such as theophylline. Leukotriene receptor antagonists have advantages in that they are relatively safe and are convenient to administer, but the use thereof is limited to an adjunctive therapy for inhalation drugs due to their relatively weak efficacy. Theophylline acts as both a non-specific adenosine receptor antagonist and a non-specific phosphodiesterase inhibitor. These targets are known to have anti-inflammatory activity and bronchodilation activity, but the use thereof is limited, because they have cardiovascular-related side effects due to nonspecific inhibition and significantly interact with other drugs due to the characteristics of xanthine-based compounds. As the adenosine receptors, a total of four types (A1, A2A, A2B, and A3) present. It is known that cardiovascular-related side effects are caused by A2A, and A1, A2B and A3 antagonists show bronchodilation activity and anti-inflammatory activity, whereas A2A agonists have bronchodilation activity and anti-inflammatory effects. Thus, studies have been actively conducted on drugs that selectively inhibit A2B or A3 as a substitute for theophylline that non-specifically inhibits adenosine receptors, but these drugs have not yet been commercialized (Wilson, C. N. British journal of pharmacology, 155(4), 475-486, 2008).

Meanwhile, the inhibition of phosphodiesterase-4 (PDE4) also is known to have anti-inflammatory activity and bronchodilation activity, and roflumilast (brand name: Daxas), a selective inhibitor of PDE4, was approved as a therapeutic agent for severe chronic obstructive pulmonary disease (COPD) and is currently used worldwide.

However, oral therapeutic agents that may be currently used for respiratory diseases such as asthma are very limited. Thus, there is a need to develop drugs having ensured safety and improved efficacy. In addition, herbal extracts having characteristics of multiple components/multiple mechanisms so as to satisfy both anti-inflammatory effects and bronchodilation effects are considered as suitable materials in the treatment of respiratory diseases.

The *Justicia* genus of the family Acanthaceae is consists of about 600 species. Typical plants belonging to the *Justicia* genus include *Justicia procumbens* L., *Justicia pectoralis*, *Justicia gendarussa*, *Justicia anselliana*, and *Justicia adhatoda*. Plants belonging to the *Justicia* genus are known to have various physiological activities, including anti-viral activity, but studies on active ingredients showing the respective physiological activities have not yet been sufficient. Among these plants, *Justicia procumbens* L. is an annual plant and is distributed in Korea, Japan, China, India, etc. Regarding the pharmacological activities of *Justicia procumbens* L., a methanol extract of the whole plant is known to have an activity of inhibiting rabbit platelet aggregation and cancer cell proliferation, and a methanol extract of the aerial part is known to have the effect of inhibiting vesicular stomatitis virus. However, the effect of *Justicia procumbens* L. on the treatment of respiratory diseases is not yet known.

DISCLOSURE

Technical Problem

It is an object of the present invention a pharmaceutical composition for preventing or treating respiratory disease, and a food composition for preventing or improving respiratory disease, which comprise an alcohol or organic solvent extract of *Justicia procumbens* L. as an active ingredient.

Another object of the present invention is to provide a pharmaceutical composition for preventing or treating respiratory disease, and a food composition for preventing or improving respiratory disease, which comprise an alcohol or organic solvent extract of *Justicia procumbens* L., the extract comprising any one or more of justicidin A, justicidin B, justicidin C, and phyllamyricin C.

Still another object of the present invention is to provide a pharmaceutical composition for preventing or treating respiratory disease, and a food composition for preventing or improving respiratory disease, which comprise an alcohol or organic solvent extract of *Justicia procumbens* L., the extract comprising: justicidin B; and any one or more of justicidin A, justicidin C, and phyllamyricin C.

Still another object of the present invention is to provide a pharmaceutical composition for preventing or treating respiratory disease, and a food composition for preventing or improving respiratory disease, which comprise an alcohol or organic solvent extract of *Justicia procumbens* L., the extract comprising: justicidin A; and any one or more of justicidin B, justicidin C, and phyllamyricin C.

Still another object of the present invention is to provide a pharmaceutical composition for preventing or treating respiratory disease, and a food composition for preventing or improving respiratory disease, which comprise an alcohol or organic solvent extract of *Justicia procumbens* L., the extract comprising justicidin B in an amount of 1 mg/g to 200 mg/g.

Still another object of the present invention is to provide a pharmaceutical composition for preventing or treating respiratory disease, and a food composition for preventing or improving respiratory disease, which comprise an alcohol or organic solvent extract of *Justicia procumbens* L., the extract comprising justicidin A in an amount of 1 mg/g to 200 mg/g.

Still another object of the present invention is to provide a pharmaceutical composition for preventing or treating respiratory disease, and a food composition for preventing or improving respiratory disease, which comprise an alcohol or organic solvent extract of *Justicia procumbens* L., the extract comprising justicidin B in an amount of 1 mg/g to 200 mg/g and justicidin A in an amount of 1 mg/g to 200 mg/g.

Technical Solution

To achieve the above objects, the present invention provides a pharmaceutical composition for preventing or treating respiratory disease, which comprises an alcohol or organic solvent extract of *Justicia procumbens* L. (=*Rostellularia procumbens* (L.) Nees) as an active ingredient.

In the present invention, *Justicia procumbens* L. is an annual plant. *Justicia procumbens* L. It has a height of about 30 cm, and its leaves are opposite leaves, long oval in shape, 2-4 cm in length, and 1-2 cm in width. In addition, both ends of the leaf are pointed, and the edges of the leaf are flat or have a wave shape. The flower of a plant is light magenta in color, blooms in July to September, and bears fruit in September to October. The whole plant of *Justicia procumbens* L. is harvested in the fall season and is used after drying. It was reported that the whole plant of *Justicia procumbens* L. has effects on heat clearance, detoxification, dampness removal, blood circulation activation, and pain alleviation, and can be used against bacterial diarrhea, jaundice, nephritis edema, muscle and bone pain, contusions, etc.

As *Justicia procumbens* L. of the present invention, a naturally occurring plant or a purchased or cultivated plant may be used without limitation. The plant includes, without limitation, all the parts thereof, including the whole plant, aerial part, leaf, root, stem, flower, seed and the like. Preferably, the whole plant, aerial part, or leaf and flower of the plant is used.

The "extract" in the present invention refers to a substance obtained by isolation from *Justicia procumbens* L. Specifically, the extract may comprise an alcohol or organic solvent extract. Preferably, it may be an alcohol or organic solvent extract, a crude extract, or a concentrate thereof. The alcohol may be a lower alcohol having 1 to 4 carbon atoms, and the organic solvent may be one or more selected from the group consisting of hexane, ethyl acetate, dichloromethane, ether, chloroform, and acetone. The lower alcohol having 1 to carbon atoms is preferably one or more selected from the group consisting of, for example, methanol, ethanol, propanol, isopropanol, butanol and n-butanol, and may most preferably be ethanol. Furthermore, the lower alcohol having 1 to 4 carbon atoms may comprise an anhydrous or hydrated alcohol. The alcohol, for example, preferably ethanol, may be 1 to 100% (v/v %), preferably 30 to 100% (v/v %), or 50% to 100% (v/v %), more preferably 70 to 100% (v/v %), even more preferably 30% (v/v %), 50% (v/v %), 70% (v/v %), or 100% (v/v %) ethanol.

The extract of the present invention may include not only an extract obtained using the above-described extraction solvent, but also an extract subjected to a conventional purification process. For example, fractions obtained through various additional purification methods, such as separation with an ultrafiltration membrane having a given molecular weight cut-off, separation by various chromatography systems (manufactured for separation according to size, charge, hydrophobicity or affinity), are also included in the scope of the extract of the present invention.

In addition, the extract of the present invention may be prepared into powder by additional processes such as Vacuum-drying and freeze-drying or spray-drying.

The extract of *Justicia procumbens* L. according to the present invention may be prepared by a process comprising the following steps, but is not limited thereto:

1) a step of shade-drying and crushing *Justicia procumbens* L.;

2) a step of extracting the crushed *Justicia procumbens* L. to obtain an extract; and 3) a step of filtering the extract, followed by concentration under reduced pressure.

As *Justicia procumbens* L. that is used in step 1, a naturally occurring plant, a cultivated plant or a commercially available plant may be used without limitation.

For the extraction in step 2), dipping (cold or hot extraction) extraction, hot-water extraction, ultrasonic extraction, supercritical extraction or reflux cooling extraction may be used without limitation. Preferably, dipping extraction, ultrasonic extraction or reflux cooling extraction is used. The extraction may be performed at a temperature of 15 to 100° C., preferably 15 to 80° C. The extraction may be performed for 1 to 72 hours, preferably 2 to 48 hours. In addition, the extraction of the present invention may be performed 1 to 5 times, preferably 2 or 3 times, depending on extraction efficiency, but is not limited thereto.

The crude extract of *Justicia procumbens* L., obtained as described above, may be prepared into powder by removing the remaining lower alcohol and organic solvent by use of a conventional drying method such as Vacuum-drying, spray-drying or freeze-drying so as to be suitable for use as a raw material for a medical drug.

The alcohol or organic solvent extract of *Justicia procumbens* L. according to the present invention can inhibit the abnormal overproliferation of spleen cells, inhibit the secretion of inflammatory cytokines, and exhibits an expectorant effect and an airway constriction inhibitory effect. Thus, it can effectively prevent, treatment or improve respiratory disease.

In the present invention, the respiratory disease may include, without limitation, various diseases caused by various factors, and may preferably be one or more selected from the group consisting of cold, pneumonia, bronchitis, asthma, allergic rhinitis, and chronic obstructive pulmonary disease. Specifically, the asthma may be allergic asthma or non-allergic asthma.

In the present invention, "preventing" refers to all actions that inhibit or delay respiratory disease by administering the composition comprising the alcohol or organic solvent extract of *Justicia procumbens* L. In the present invention, "treating" refers to all actions that alleviate or beneficially change the symptoms of disease by administering the composition comprising the alcohol or organic solvent extract of *Justicia procumbens* L.

In addition, the alcohol or organic solvent extract of *Justicia procumbens* L. is characterized by comprising any one or more of justicidin A, justicidin B, justicidin C, and phyllamyricin C.

Therefore, the present invention provides a pharmaceutical composition for preventing or treating respiratory disease, which comprises justicidin A, justicidin B, or a mixture thereof.

The present invention also provides a pharmaceutical composition for preventing or treating respiratory disease, which comprises an alcohol or organic solvent extract of *Justicia procumbens* L., the extract comprising any one or more of justicidin A, justicidin B, justicidin C, and phyllamyricin C.

The present invention also provides a pharmaceutical composition for preventing or treating respiratory disease, which comprises an alcohol or organic solvent extract of *Justicia procumbens* L., the extract comprising: justicidin B; and any one or more of justicidin A, justicidin C, and phyllamyricin C.

The present invention also provides a pharmaceutical composition for preventing or treating respiratory disease, which comprises an alcohol or organic solvent extract of *Justicia procumbens* L., the extract comprising: justicidin A; and any one or more of justicidin B, justicidin C, and phyllamyricin C.

The justicidin A, justicidin B, justicidin C and phyllamyricin C are the active substances in the extract of *Justicia procumbens* L., and these active substances exhibit the effects of preventing, improving and treating respiratory disease. The alcohol or organic solvent extract of *Justicia procumbens* L. comprises one or more of these active substances individually or in combination. Preferably, it essentially comprises justicidin B and optionally comprises one or more of the remaining three compounds (justicidin A, justicidin C, and phyllamyricin C), or essentially comprises justicidin A and optionally comprises one or more of the remaining three compounds (justicidin B, justicidin C, and phyllamyricin C), and thus exhibits excellent effects of preventing, improving or treating respiratory disease.

In the present invention, the justicidin A, justicidin B, justicidin C and phyllamyricin C may be isolated from the alcohol or organic solvent extract of *Justicia procumbens* L., and the detailed structures thereof are shown in FIG. 1. (Compound 1: justicidin B; Compound 2: justicidin A; Compound 3: justicidin C; and Compound 4: phyllamyricin C).

In one specific preparation example, justicidin A, justicidin B, justicidin C and phyllamyricin C were isolated from an ethanol extract of *Justicia procumbens* L. In one specific example, it was confirmed that the above-described four compounds were present in methanol, isopropanol and ethanol extracts of *Justicia procumbens* L., whereas the four compounds were not detected in a water extract of *Justicia procumbens* L.

When each of the justicidin A, justicidin B, justicidin C and phyllamyricin C of the present invention is used as a single compound, it has the ability to inhibit spleen cell proliferation and the ability to inhibit IL4 and IL5 secretion. In particular, when these compounds are used in combination, they have synergistic effects on the inhibition of spleen cell proliferation and the inhibition of IL4 and IL5 secretion.

In one specific example, justicidin B was combined with one or more compounds of justicidin A, justicidin C and phyllamyricin C, and the ability of the combination to inhibit spleen cell proliferation and the ability of the combination to inhibit IL4 and IL5 secretion were evaluated in various manners. As a result, it could be seen that treatment with the combination showed significantly better spleen cell proliferation inhibitory ability and IL4 and IL5 secretion inhibitory ability than treatment with each of the single compounds. This can be confirmed by CI values all calculated to be less than 1. (Example 2).

The justicidin A, Justicidin B, justicidin C and phyllamyricin C of the present invention are preferably contained in the alcohol or organic solvent extract of *Justicia procumbens* L. in an amount of 1 mg/g to 200 mg/g based on the extract.

More preferably, in the alcohol or organic solvent extract of *Justicia procumbens* L. of the present invention, the justicidin B may be contained in an amount of 1 mg/g to 200 mg/g based on the extract.

Furthermore, in the alcohol or organic solvent extract of *Justicia procumbens* L. of the present invention, the justicidin A may be contained in an amount of 1 mg/g to 200 mg/g based on the extract.

Moreover, when justicidin A and justicidin B are contained in the composition of the present invention, they may be contained at a ratio of 10:1 to 1:1. Specifically, they may be contained at ratios of 9:1, 8:1, 7:1, 6:1, 5:1, 4:1, 3:1 and 2:1.

Moreover, when justicidin A and justicidin C are contained in the composition of the present invention, they may be contained at a ratio of 10:1 to 5:1. Specifically, they may be contained at ratios of 9:1, 8:1, 7:1 and 6:1. The justicidin A may be justicidin B, and the justicidin C may be phyllamyricin C.

The alcohol or organic solvent extract of *Justicia procumbens* L. of the present invention exhibits excellent effects on the prevention, improvement and treatment of respiratory disease by comprising the justicidin A, justicidin B, justicidin C or phyllamyricin C as an active ingredient in the above-described amount.

Preferably, in the alcohol or organic solvent extract of *Justicia procumbens* L. of the present invention, which comprises one or more of justicidin A, justicidin B, justicidin C and phyllamyricin C individually or in combination, the *Justicia procumbens* L. may be any one or more selected from the group consisting of the whole plant, aerial part, root, leaf, flower and seed thereof, and may preferably be the atrial part of *Justicia procumbens* L. The alcohol extract of *Justicia procumbens* L. may be an extract obtained by extraction with a lower alcohol having 1 to 4 carbon atoms, for example, ethanol, more preferably 30%, 50%, 70% or 100% ethanol, and the organic solvent extract of *Justicia procumbens* L. may be an extract obtained by extraction with hexane, ethyl acetate, dichloromethane, ether, chloroform or acetone.

The alcohol or organic solvent extract of *Justicia procumbens* L. as described above may be used alone or in a mixture with one or more pharmaceutical drugs or herbal agents known to effective against respiratory diseases. When the extract of the present invention is used in a mixture with an extract of other plant, the other plant may be extracted after being mixed with *Justicia procumbens* L. or may be mixed with *Justicia procumbens* L. after being extracted separately.

The pharmaceutical composition of the present invention may be formulated in the form of tablet, pill, powder, granule, capsule, suspension, solution, emulsion, syrup, aerosol, injectable solution or the like according to a conventional method for preventing and treating respiratory disease. Examples of carriers, excipients and diluents which may be contained in the pharmaceutical composition of the present invention include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil. The composition of the present invention may be formulated with conventional diluents or excipients, such as fillers, extenders, binders, wetting agents, disintegrants, surfactants, etc., which are generally used.

Solid formulations for oral administration include tablets, pills, powders, granules, capsules and the like, and such solid formulations may comprise at least one excipient, for example, starch, calcium carbonate, sucrose, lactose, gelatin or the like. In addition to simple excipients, lubricants such as magnesium stearate or talc may also be used. Liquid formulations for oral administration include suspensions, solutions, emulsions, and syrup, and may contain various excipients, for example, wetting agents, flavoring agents, aromatics and preservatives, in addition to water and liquid paraffin, which are frequently used simple diluents.

Formulations for parenteral administration include sterilized aqueous solutions, non-aqueous solutions, suspensions, emulsions, freeze-dried preparations, suppositories, etc. As non-aqueous solvents or suspending agents, propylene glycol, polyethylene glycol, plant oils such as olive oil, injectable esters such as ethyl oleate, and the like can be used.

In addition, the pharmaceutical composition of the present invention may further comprise carriers, excipients or diluents. The carriers, excipients or diluents that may be used include lactose, dextrose, sucrose, sorbitol, mannitol, xylitol, erythritol, maltitol, starch, acacia rubber, alginate, gelatin, calcium phosphate, calcium silicate, cellulose, methyl cellulose, hydroxypropyl methyl cellulose, microcrystalline cellulose, polyvinyl pyrrolidone, water, methylhydroxy benzoate, propylhydroxy benzoate, minerals such as talc, magnesium stearate or silicon dioxide, and the like.

The pharmaceutical composition of the present invention should be administered in a pharmaceutically effective amount. The "pharmaceutically effective amount" refers to an amount sufficient to treat diseases, at a reasonable benefit/risk ratio applicable to any medical treatment. The effective dosage level of the composition may be determined by a person skilled in the art depending on various factors, including a formulation method, the patient's condition, body weight, sex and age, the severity of the disease, the form of drug, the route and duration of administration, excretion rate, and reaction sensitivity. As recognized by those skilled in the art, the effective amount may vary depending on the route of treatment, the use of excipients and the possibility of use with other drugs.

The dose or dosage of the alcohol or organic solvent extract of *Justicia procumbens* L. according to the present invention may vary depending on the patient's body weight, age, sex, health condition, diet, the time of administration, the mode of administration, excretion rate, and the severity of the disease. However, the extract of the present invention is administered at a dose of 0.001 mg/kg to 1000 mg/kg once or several times a day for adults.

The pharmaceutical composition of the present invention may be administered via various routes to mammals, including mice, livestock and humans. For example, it may be administered orally, parenterally, intravenously, intradermally or by subcutaneous injection.

In another aspect, the present invention provides a method for preventing or treating respiratory disease, the method comprising a step of administering to a subject in need thereof a pharmaceutical composition comprising an alcohol or organic solvent extract of *Justicia procumbens* L.

The administration may be performed orally, parenterally, intravenously, intradermally or by subcutaneous injection. When the extract is to be administered to a subject, it may be administered in an effective amount required for the prevention or treatment of allergic disease. When the alcohol or organic solvent extract of *Justicia procumbens* L. is administered to a subject, the symptoms of respiratory-related disease in the subject can be inhibited. The respiratory disease that may be prevented or treated by the administration may include, without limitation, various diseases caused by various stimuli. Preferably, the respiratory disease may be one or more selected from the group consisting of cold, pneumonia, bronchitis, asthma, allergic rhinitis, and chronic obstructive pulmonary disease.

In the present invention, the subject refers to an animal. Specifically, the subject is a mammal in which prevention or treatment with the extract of the present invention can exhibit a beneficial effect. Preferred examples of the subject include Primates such as humans. In addition, such subjects include all subjects having allergic symptoms or being at risk of developing such symptoms. An amount effective for the prevention or treatment of respiratory disease refers to an amount that provides, in single or multiple doses, alone or in combination with one or more other compositions (other therapeutic agents against respiratory diseases), a desired outcome in or a benefit to a subject.

In another aspect, the present invention provides a food composition for preventing or improving respiratory disease, which comprises an alcohol or organic solvent extract of *Justicia procumbens* L. as an active ingredient.

The present invention also provides a food composition for preventing or improving respiratory disease, which comprises an alcohol or organic solvent extract of *Justicia procumbens* L., the extract comprising any one or more of justicidin A, justicidin B, justicidin C, and phyllamyricin C.

The present invention also provides a food composition for preventing or improving respiratory disease, which comprises an alcohol or organic solvent extract of *Justicia procumbens* L., the extract comprising: justicidin B; and any one or more of justicidin A, justicidin C, and phyllamyricin C.

The present invention also provides a food composition for preventing or improving respiratory disease, which comprises an alcohol or organic solvent extract of *Justicia procumbens* L., the extract comprising: justicidin A; and any one or more of justicidin B, justicidin C, and phyllamyricin C.

The present invention also provides a food composition for preventing or improving respiratory disease, which comprises justicidin A, justicidin B, or a mixture thereof.

The present invention also provides a food composition for preventing or improving respiratory disease, which comprises an alcohol or organic solvent extract of *Justicia procumbens* L., the extract comprising justicidin B in an amount of 1 mg/g to 200 mg/g.

The present invention also provides a food composition for preventing or improving respiratory disease, which comprises an alcohol or organic solvent extract of *Justicia procumbens* L., the extract comprising justicidin A in an amount of 1 mg/g to 200 mg/g.

The present invention also provides a food composition for preventing or improving respiratory disease, which comprises an alcohol or organic solvent extract of *Justicia procumbens* L., the extract comprising justicidin B in an amount of 1 mg/g to 200 mg/g and justicidin A in an amount of 1 mg/g to 200 mg/g.

When the alcohol or organic solvent extract of *Justicia procumbens* L., which is contained in the food composition of the present invention, is administered together with a food, it can inhibit abnormal overproliferation of spleen cells, can inhibit the secretion of Th2 inflammatory cytokines, and can effectively inhibit mucus secretion and airway constriction, indicating that it exhibits an excellent effect of improving respiratory disease. Accordingly, it can effectively prevent or improve respiratory disease.

The food composition may be a functional food according to the purpose of the present invention. Therefore, the present invention provides a food composition for preventing or improving respiratory disease, wherein the food is a functional health food.

The functional food is a food designed to help regulate the body's natural biorhythms. It is a food given added value by physical, biochemical and bioengineering techniques so that it can act to express the functions of a given food for a particular purpose. This functional food is a processed food designed to defend the body, help regulate the body's natural biorhythms, prevent diseases and help a person recover from diseases. It may contain food-acceptable additives, sweeteners or functional materials.

Examples of the food composition according to the present invention include various foods, for example, beverages, gums, teas, vitamin complexes, health supplement foods, etc. The beverages include natural fruit juice, fruit juice beverages, vegetable beverages, etc. The food composition of the present invention may be formulated as tablets, granules, powders, capsules, liquid solutions, pills or the like according to known methods.

In addition, the food composition of the present invention may further comprise various conventional flavorings, natural carbohydrates, etc. Examples of the flavorings include natural flavorings such as thaumatin or *stevia* extracts, and synthetic flavorings such as saccharin, aspartame, etc. Examples of the natural carbohydrates include monosaccharides such as glucose or fructose, disaccharides such as maltose or sucrose, polysaccharides such as dextrin or cyclodextrin, sugar alcohols such as xylitol, sorbitol or erythritol, and the like. In addition the food composition of the present invention may further comprise food-acceptable additives, including various nutrients, vitamins, minerals (electrolytes), colorants, pectic acid and its salt, alginic acid and its salt, organic acids such as anhydrous citric acid, protective colloidal thickeners, pH adjusting agents, stabilizers, preservatives, glycerin, alcohol, carbonizing agents as used in carbonated beverages, fruit flesh for preparation of natural fruit juice, fruit juice beverages or vegetable juices, etc. Such additives may be used alone or in combination.

In still another aspect, the present invention provides the use of an alcohol or organic solvent extract of *Justicia procumbens* L. for the prevention or treatment of respiratory disease.

In still another aspect, the present invention provides the use of an alcohol or organic solvent extract of *Justicia procumbens* L. in manufacture of a medicament for preventing or treating respiratory disease.

The alcohol or organic solvent extract of *Justicia procumbens* L. for manufacture of the medicament may be mixed with pharmaceutically acceptable carriers, excipients and diluents, etc., and may be prepared as a combination formulation with other active agents so as to exhibit synergistic effects.

It should be understood that the values described in the specification include equivalents thereof unless otherwise specified.

Advantageous Effects

The alcohol or organic solvent extract of *Justicia procumbens* L. according to the present invention, or justicidin A, justicidin B, justicidin C and phyllamyricin C, and the alcohol or organic solvent extracts of *Justicia procumbens* L. comprising the same, can inhibit the growth of spleen cells that cause immune responses, can inhibit Th2 cytokines associated with asthma, show expectorant effects in ICR mice, and exhibit the effect of inhibiting methacholine-induced airway resistance in Balb/c mice. Thus, they may be widely used as an agent for preventing or treating respiratory disease or as an agent for preventing or improving respiratory disease.

DESCRIPTION OF DRAWINGS

FIG. 1 shows the chemical structures of compounds 1 to 4 isolated from an extract of *Justicia procumbens* L. according to the present invention. (compound 1: justicidin B; compound 2: justicidin A; compound 3: justicidin C; and compound 4: phyllamyricin C).

FIG. 2 shows the results of HPLC of a water extract and ethanol extract of *Justicia procumbens* L. according to the present invention.

FIG. 3 shows the results of HPLC of other alcohol extracts of *Justicia procumbens* L. according to the present invention.

FIG. 4 shows the results of airway hypersensitivity for an ethanol extract of *Justicia procumbens* L. according to the present invention.

FIG. 5 shows the results of lung tissue staining for an ethanol extract of *Justicia procumbens* L. according to the present invention.

FIG. 6 shows the results of lung tissue staining for a mixture of an ethanol extract of *Justicia procumbens* L. according to the present invention and colloidal silicon dioxide.

BEST MODE

Hereinafter, preferred Preparation Examples, Examples and Formulation Examples will be described for a better understanding of the present invention. It is to be understood, however, that these Preparation Examples, Examples and Formulation Examples are for illustrative purposes only and are not intended to limit the scope of the present invention.

Preparation Example 1: Preparation of *Justicia procumbens* L. Extract

*Justicia procumbens* L. used in the experiment was cultivated and harvested in Jecheon-si, Chungcheongbuk-do, South Korea, and dried and cut. The origin of the plant was identified by the National Institute of Biological Resources of the Ministry of Environment (Korea) (identification sample number: NIBRVP0000530742). Using water and organic solvents (ethanol or other alcohols) as extraction solvents, *Justicia procumbens* L. extracts were prepared.

Preparation Example 1-1: Preparation of Water Extract of *Justicia procumbens* L.

The above-ground part of *Justicia procumbens* L. dried in the shade was cut to a size of about 1 to 2 cm, and about 10 g of the cut plant was taken exactly and extracted under reflux with 100 ml of purified water in a constant-temperature incubator (D-6, Hansol Science) at 80° C. twice (first extraction: 2 hours, and second extraction: 1 hour). The extract was naturally filtered through filter paper, and the filtrate was concentrated with a vacuum evaporator (N-1100, EYELA) at 60° C., and then dried in a vacuum oven (OV-12, JEIO Tech) at 60° C. for 12 hours, thereby obtaining 1.64 g of a water extract of *Justicia procumbens* L.

Preparation Example 1-2: Preparation of Ethanol Extracts and Other Alcohol Extracts of *Justicia procumbens* L.

Ethanol extracts and other alcohol extracts of *Justicia procumbens* L. were prepared in the same manner as described in Preparation Example 1-1, except for the weight of herbal material (above-ground part of *Justicia procumbens* L.) used and extraction solvents. Specifically, ethanol extracts of *Justicia procumbens* L. were prepared by extracting the above-ground part of *Justicia procumbens* L. with varying concentrations (30%, 50%, 70%, and 100% (v/v %)) of ethanol. In addition, using isopropanol and methanol, alcohol extracts of *Justicia procumbens* L. were prepared.

Preparation Example 1-3: Preparation of Ethanol Extract of Each Part of *Justicia procumbens* L.

The above-ground part of *Justicia procumbens* L. dried in the shade was divided into an aerial part, a stem, and a leaf and a flower, and then pulverized using a pulverizer (KSP-35, Korea Medi Co., Ltd.). About 5 g of each part of the crushed *Justicia procumbens* L. was taken exactly and extracted ultrasonically (UG 600, Hanil Ultrasonic) with 100 ml of ethanol, and each of the filtrates was dried in a vacuum oven (OV-12, JEIO Tech) at 60° C. for 12 hours, thereby preparing ethanol extracts.

Preparation Example 1-4: Preparation of Ethanol Extracts of *Justicia procumbens* L. By Various Extraction Methods The aerial part of *Justicia procumbens* L. dried in the shade was cut to a size of about 1 to 2 cm, and about 5 g of the cut plant was taken exactly and extracted with 100 ml of varying concentrations (30%, 50%, 70%, and 100% (v/v %)) of an ethanol solvent by ultrasonic extraction (1 hour) and dipping extraction (5 hours). Then, each of the filtrates was dried in a vacuum dryer (OV-12, JEIO Tech) at 60° C. for 12 hours, thereby preparing each extract.

Preparation Example 2: Isolation and Preparation of Active Substances 480 g of the aerial part of *Justicia procumbens* L., cut to a size of about 1 to 2 cm and dried in the shade, was extracted under reflux with 3 L of ethanol in a constant-temperature incubator (J-BAL, DISCO) at 80° C. twice (first extraction: 2 hours, and second extraction: 1 hour). The extract was filtered under reduced pressure at a temperature of 50 to 60° C., and then concentrated with a vacuum evaporator (N-1100, EYELA), thereby obtaining about 11.44 g (2.4% yield) of an ethanol concentrate. The ethanol concentrate was suspended in 1 L of distilled water, and then subjected to solvent fractionation three times with 1 L of n-hexane. The prepared n-hexane fraction (about 5 g) was subjected to silica gel column chromatography using a concentration gradient solvent system comprising dichloromethane and methanol as a mobile phase solvent, thereby preparing a total of 11 sub-fractions (JP-Hex-01 to 11). Among these sub-fractions, sub-fraction No. 4 (JP-Hex-04) was subjected again to silica gel column chromatography using methylene chloride and methanol as a mobile phase solvent, thereby preparing 9 sub-fractions (JP-Hex-0401 to 0409). Among them, final sub-fraction No. 4 (JP-Hex-0404) was subjected to reverse-phase preparative high-performance chromatography using 70% methanol, thereby isolating and preparing each of compound (justicidin B) with a retention time of 8.1 min, compound 2 (justicidin A) with a retention time of 10.2 min, and compound 3 (justicidin C) with a retention time of 14.3 min.

In addition, sub-fraction No. 6 (JP-Hex-06) was subjected to silica gel column chromatography using n-hexane and ethyl acetate as a mobile phase solvent, thereby preparing 19 sub-fractions (JP-Hex-0601 to 0619). Among them, sub-fraction No. (JP-Hex-0606) was subjected to reverse-phase preparative high-performance chromatography using 70% methanol, thereby preparing compound 4 (phyllamyricin C) with a retention time of 14.7 min.

The structural analysis of compounds 1 to 4 isolated as described above was performed, and the results were confirmed through each literature. The identified chemical structures of compounds 1 to 4 are shown in FIG. 1.

Compound 1 (justicidin B): $^1$H-NMR (CDCl$_3$, 500 MHz) δ 7.70 (1H, s, H-1), 7.18 (1H, s, H-8), 7.11 (1H, s, H-5), 6.97 (1H, d, J=8.0 Hz, H-5'), 6.86 (1H, d, J=1.5 Hz, H-2'), 6.83 (1H, dd, J=1.5, 8.0 Hz, H-6'), 6.09 (1H, d, J=22.4 Hz, O—CH$_2$—O), 6.05 (1H, d, J=22.4 Hz, O—CH$_2$—O), 5.38 (2H, s, H-2a), 4.05 (3H, s, 7-OCH$_3$), 3.81 (3H, s, 6-OCH$_3$). $^{13}$C-NMR (CDCl$_3$, 125 MHz) δ 170.0 (C-3a), 151.9 (C-7), 150.2 (C-6), 147.6 (C-3), 147.6 (C-4), 139.8 (C-2), 139.6 (C-4), 133.3 (C-8a), 128.9 (C-4a), 128.5 (C-1), 123.6 (C-6), 118.6 (C-3), 118.4 (C-1), 110.7 (C-2), 108.3 (C-5), 106.1 (C-8), 106.0 (C-5), 101.3 (O—CH$_2$—O), 68.1 (C-2a), 56.1 (7-OCH$_3$), 55.9 (6-OCH$_3$). From these results, compound 1 was identified as justicidin B, and these results were consistent with the results shown in *Journal of Natural Products*, Vol. 58, No 2, 244-249, 1995.

Compound 2 (justicidin A): $^1$H-NMR (CDCl$_3$, 500 MHz) δ 7.54 (1H, s, H-8), 7.06 (1H, s, H-5), 6.95 (1H, d, J=7.7 Hz, H-5), 6.82 (1H, d, J=1.5 Hz, H-2), 6.79 (1H, dd, J=1.5, 7.7 Hz, H-6), 6.09 (1H, d, J=22.3 Hz, O—CH$_2$—O), 6.04 (1H, d, J=22.3 Hz, O—CH$_2$—O), 5.54 (2H, s, H-2a), 4.13 (3H, s, 1-OCH$_3$), 4.07 (3H, s, 7-OCH$_3$), 3.80 (3H, s, 6-OCH$_3$). $^{13}$C-NMR (CDCl$_3$, 125 MHz) δ 169.7 (C-3a), 151.7 (C-7), 150.4 (C-6), 147.9 (C-1), 147.6 (C-3), 147.5 (C-4), 134.5 (C-4), 130.7 (C-4a), 128.6 (C-1), 126.1 (C-8a), 124.6 (C-2), 123.7 (C-6), 119.4 (C-3), 110.8 (C-2), 108.3 (C-5), 106.3 (C-5), 101.3 (O—CH$_2$—O), 100.7 (C-8), 66.7 (C-2a), 59.7 (1-OCH$_3$), 56.2 (7-OCH$_3$), 55.9 (6-OCH$_3$). From these results, compound 2 was identified as justicidin A, and these results were consistent with the results shown in *Journal of Natural Products*, Vol. 62, 1056-1058, 1999.

Compound 3 (justicidin C): $^1$H-NMR (CDCl$_3$, 500 MHz) δ 7.69 (1H, s, H-8), 6.98 (1H, s, H-5), 6.96 (1H, d, J=7.7 Hz, H-5), 6.81 (1H, d, J=1.7 Hz, H-2), 6.80 (1H, dd, J=1.7, 7.7 Hz, H-6), 6.09 (1H, d, J=16.4 Hz, O—CH$_2$—O), 6.06 (1H, d, J=16.4 Hz, O—CH$_2$—O), 5.13 (2H, s, H-3a), 4.37 (3H, s, 1-OCH$_3$), 4.06 (3H, s, 7-OCH$_3$), 3.83 (3H, s, 6-OCH$_3$). $^{13}$C-NMR (CDCl$_3$, 125 MHz) δ 169.4 (C-2a), 155.5 (C-1), 152.5 (C-6), 149.9 (C-7), 148.4 (C-3), 147.6 (C-4), 139.1 (C-3), 133.5 (C-4a), 129.8 (C-1), 126.5 (C-4), 123.7 (C-8a), 123.0 (C-6), 109.9 (C-2), 109.5 (C-2), 109.1 (C-5), 104.2 (C-5), 102.4 (C-8), 101.5 (O—CH$_2$—O), 68.9 (C-3a), 63.6 (1-OCH$_3$), 56.2 (7-OCH$_3$), 56.0 (6-OCH$_3$). From these results, compound 3 was identified as justicidin C, and these results were consistent with the results shown in *Tetrahedron Letters*, No. 12, pp. 923-925, 1970.

Compound 4 (phyllamyricin C): $^1$H-NMR (CDCl$_3$, 500 MHz) δ 7.69 (1H, s, H-5), 6.98 (1H, s, H-1), 6.96 (1H, d, J=7.8 Hz, H-5), 6.81 (1H, d, J=1.8 Hz, H-2), 6.80 (1H, dd, J=1.8, 7.8 Hz, H-6), 6.09 (1H, d, J=16.4 Hz, O—CH$_2$—O), 6.06 (1H, d, J=16.4 Hz, O—CH$_2$—O), 5.13 (2H, s, H-2a), 4.37 (3H, s, 6-OCH$_3$), 4.06 (3H, s, 8-OCH$_3$), 3.83 (3H, s, 7-OCH$_3$). $^{13}$C-NMR (CDCl$_3$, 125 MHz) δ 169.3 (C-3a), 155.5 (C-6), 152.5 (C-7), 149.9 (C-8), 148.4 (C-3), 147.6 (C-4), 143.5 (C-4), 139.1 (C-2), 133.5 (C-8a), 129.8 (C-1), 126.4 (C-3), 123.7 (C-4a), 123.0 (C-6), 109.9 (C-2), 109.1 (C-5), 104.2 (C-1), 102.4 (C-5), 101.5 (O—CH$_2$—O) 68.9 (C-2a), 63.6 (6-OCH$_3$), 56.2 (8-OCH$_3$), 56.0 (7-OCH$_3$). From these results, compound 4 was identified as phyllamyricin C, and these results were consistent with the results shown in *Journal of Natural Products*, Vol. 58, No 2, 244-249, 1995.

Among the isolated active ingredients, justicidin B was obtained in large amounts, and a standard (purity: 95.25%) was used after its purity was confirmed by HPLC.

Preparation Example 3: Preparation of a Mixture (1:1) of 100% Ethanol Extract of *Justicia procumbens* L. And Colloidal Silicon Oxide About 400 kg of *Justicia procumbens* L., crushed to a size of about 1 cm, was extracted by dipping in 4000 L of 100% ethanol at room temperature (25° C.) for 24 hours, and then filtered under reduced pressure. The residue was extracted again by dipping in 3200 L of 100% ethanol at room temperature (25° C.) for 24 hours, and then filtered under reduced pressure. The filtrate was concentrated under reduced pressure at 60° C., thereby obtaining about 93.85 kg (3.3% yield) of an ethanol extract of *Justicia procumbens* L. having a solid content of about 14%. The same weight (about 13 kg) of colloidal silicon oxide (AEROSIL® 200, Evonik) as the solid weight of the ethanol extract of *Justicia procumbens* L. was added to the ethanol extract, stirred sufficiently, and then dried in a vacuum dryer for 72 hours. The dried mixture (1:1) of the 100% ethanol extract of *Justicia procumbens* L. and the colloidal silicon dioxide was powdered, thereby preparing about 26 kg of a mixture (1:1) of the 100% ethanol extract of *Justicia procumbens* L. and the colloidal silicon dioxide.

Example 1: High-Performance Liquid Chromatography (HPLC) Patterns and Justicidin B Contents of *Justicia procumbens* L. Extracts In order to confirm the active ingredients contained in the *Justicia procumbens* L. extracts prepared by the preparation methods of Preparation Examples 1-1 to 1-4 above, high-performance liquid chromatography (HPLC, Agilent 1260, USA) was performed under the conditions shown in Table 1 below, and the results are shown in FIGS. 2 and 3.

TABLE 1

| Detector | UV absorption spectrometer |
| Detection wavelength | UV 256 nm |
| Column | Capcellpak UG C18 (4.6 × 250 mm, 5 μm) |
| Column temperature | 35° C. |

| | <Gradient program> | | |
| --- | --- | --- | --- |
| | Time (min) | % acetonitrile | % water |
| Mobile phase | 0 | 15 | 85 |
| | 5 | 15 | 85 |
| | 40 | 46 | 54 |
| | 60 | 55 | 45 |
| | 70 | 60 | 40 |
| | 75 | 40 | 60 |
| | 76 | 15 | 85 |
| Flow rate | 0.8 mL/min | | |
| Amount injected | 10 μl | | |

The results of HPLC analysis indicated that the active ingredients were detected in all the ethanol and other alcohol extracts of *Justicia procumbens* L. Specifically, as shown in FIG. 2, in the ethanol extract of *Justicia procumbens* L., the peaks of compounds 1 to 4, which are the active ingredients, were detected at RT 46.2 min (justicidin B), RT 49.5 min (justicidin A), and RT 53.4 min (justicidin C and phyllamyricin C C). In addition, as shown in FIG. 3, in the other alcohol extracts, the peaks of compounds 1 to 4 were detected at RT 47.6 min (justicidin B), RT 51.3 min (justicidin A), and RT 55.4 min (justicidin C and phyllamyricin C).

However, justicidin B, justicidin A, justicidin C or phyllamyricin C was not detected in the water extract of *Justicia procumbens* L.

The contents of justicidin B in the water extract and ethanol extract of *Justicia procumbens* L. and in the ethanol extract of each part of *Justicia procumbens* L. were calculated using Equation 1 below, and the results are shown in Tables 2 and 3 below.

$$\text{Justicidin } B \text{ content (mg/g)} = \frac{P_t}{P_s} \times \frac{C_s}{C_t} \times P \quad \text{[Equation 1]}$$

$P_t$ and $P_s$: peak areas of justicidin B in test sample and standard sample;

$C_t$ and $C_s$: concentrations of test sample and standard sample (test sample: 0.001 g/mL, and standard sample: 0.05 mg/mL);

P: Purity (0.9525) of justicidin B.

TABLE 2

| Preparation method | Extraction solvent for *Justicia procumbens* L. | Justicidin B content (mg/g) |
|---|---|---|
| Preparation Example 1-1 | Water extract | Not detected |
| Preparation Example 1-2 | 30% ethanol extract | 3.39 |
| Reflux extraction | 50% ethanol extract | 4.76 |
| | 70% ethanol extract | 4.89 |
| | 100% ethanol extract | 49.00 |
| Preparation Example 1-4 | 30% ethanol extract | 1.18 |
| Ultrasonic extraction | 50% ethanol extract | 4.75 |
| | 70% ethanol extract | 7.70 |
| | 100% ethanol extract | 137.83 |
| Preparation Example 1-4 | 30% ethanol extract | 0.95 |
| Dipping extraction | 50% ethanol extract | 3.19 |
| | 70% ethanol extract | 6.74 |
| | 100% ethanol extract | 147.02 |

TABLE 3

| Preparation method | Extracted part of *Justicia procumbens* L. | Justicidin B content (mg/g) |
|---|---|---|
| Preparation Example 1-3 | Stem | 1.95 |
| Reflux extraction | Leaf + flower | 177.91 |
| | Aerial part | 45.69 |

In addition, for the 1:1 mixture of the 100% ethanol extract of *Justicia procumbens* L. and colloidal silicon oxide, prepared by the preparation method of Preparation Example 3 above, justicidin B was detected as described above. As a result, it was shown that the content of justicidin B was 16.87 mg/g.

Example 2: The Effects of *Justicia procumbens* L. Extracts on Inhibition of Spleen Cell Proliferation and Inhibition of Secretion of Th2 Inflammatory Cytokines In order to confirm the inflammation inhibitory effects of the *Justicia procumbens* L. extracts, splenocytes were isolated from the spleens of Balb/c mice. The isolated splenocytes were diluted in RPMI medium (containing 10% fetal bovine serum (FBS) and antibiotics (100 U/mL penicillin and 100 μg/mL streptomycin)) at a concentration of $5 \times 10^6$ cells/nit, and the cell dilution was dispended in a 24-well plate in an amount of 500 μl/well and in a 96-well plate in an amount of 100 μl/well. The plates were incubated in a 5% $CO_2$ incubator at 37° C. for 48 hours. When the spleen cells were dispensed, the cells were treated with 5 μg/mL of Concanavalin A to induce immune responses, and at the same time, the cells were treated with each of the *Justicia procumbens* L. extracts prepared in Preparation Examples 1-1 and 1-2, the active substances prepared in Preparation Example 2, and positive controls (dexamethasone and montelukast). The medium of the 24-well plate was used to measure the degree of secretion of Th2 inflammatory cytokines (IL4 and IL5), and the 96-well plate was used to measure the degree of cell proliferation. First, in order to measure Th2 cytokines, the medium in the 24-well plate was collected and centrifuged at 800×g for 5 minutes, and the supernatant was collected. 100 μl of the supernatant per well was used in IL4 or IL5 enzyme-linked immunosorbent assay (ELISA, Komabiotech Inc.) to measure the degree of secretion of these cytokines. In order to measure the degree of cell proliferation, 10 mL of CCK8 (cell counting kit 8, Donjindo) solution was added to each well of the 96-well plate, and after 4 hours, the absorbance value was measured. The degree of inhibition of spleen cell proliferation by each drug and the degree of inhibition of Th2 cytokine secretion by each drug were calculated using Equation 2 below. For drug synergistic effects, a linear equation was constructed using the concentrations of drugs administered alone as x-coordinates and using drug concentration-dependent inhibition as y-coordinates. Using this linear equation, the concentrations of drugs administered alone, which correspond to inhibition achieved when administered in combination, were calculated, and combination index (CI) was calculated using Equation 3 below. A CI value of less than 1 indicates a synergistic effect, a CI value of 1 indicates an additive effect, and a CI value of more than 1 indicates an antagonistic effect (Liang Zhao et. al., *Clinical Cancer Research*, 10, 7994-8004, 2004). The results of the measurement are shown in Tables 4 to 8 below.

$$\text{Inhibition (\%)} = \quad \text{[Equation 2]}$$
$$\{(\text{value of test group} - \text{value of normal group})/$$
$$(\text{value of induced group} -$$
$$\text{value of normal group})\} \times 100$$

$$CI = \frac{Ca}{ICa} + \frac{Cb}{ICb} + \ldots + \frac{Cx}{ICx} \quad \text{[Equation 3]}$$

Ca: concentration of drug "a" when administered in combination;

Cb: concentration of drug "b" when administered in combination;

Cx: concentration of drug "x" when administered in combination;

ICa: concentration of drug "a" administered alone, which corresponds to inhibition achieved when administered in combination;

ICb: concentration of drug "b" administered alone, which corresponds to inhibition achieved when administered in combination;

ICx: concentration of drug "x" administered alone, which corresponds to inhibition achieved when administered in combination.

TABLE 4

| Test group | Drug concentration | Inhibition of splenocyte proliferation (n = 3, Mean ± SD) |
|---|---|---|
| Water extract | 3 μg/ml | −13.0 ± 9.14 |
| 30% ethanol extract | 3 μg/ml | 7.8 ± 10.17 |
| 50% ethanol extract | 3 μg/ml | 30.4 ± 2.74 |

TABLE 4-continued

| Test group | Drug concentration | Inhibition of splenocyte proliferation (n = 3, Mean ± SD) |
|---|---|---|
| 70% ethanol extract | 3 μg/ml | 44.2 ± 2.11 |
| 100% ethanol extract | 2 μg/ml | 62.3 ± 0.83 |
|  | 4 μg/ml | 99.9 ± 1.03 |
| 100% isopropanol extract | 3 μg/ml | 43.1 ± 1.04 |
| 100% methanol | 3 μg/ml | 35.8 ± 3.06 |
| Dexamethasone (positive control) | 0.5 μM | 110.3 ± 0.62 |
| Montelukast (positive control) | 10 μM | 44.1 ± 4.34 |

TABLE 5

| Test group | Concentration (μM) | Inhibition of splenocyte proliferation (%, n = 3, Mean ± SD) | CI value |
|---|---|---|---|
| Justicidin A (JA) | 0.5 | -2.7 ± 1.84 | — |
|  | 1 | 9.4 ± 4.36 | — |
|  | 2.5 | 56.4 ± 18.80 | — |
|  | 5 | 85.0 ± 2.43 | — |
| Justicidin B (JB) | 0.25 | 14.2 ± 1.43 | — |
|  | 0.5 | 64.3 ± 0.50 | — |
| Justicidin C (JC) | 0.5 | -3.6 ± 4.00 | — |
|  | 5 | 8.4 ± 3.20 | — |
| Phyllamyricin C (PC) | 0.5 | 0.9 ± 2.86 | — |
|  | 5 | 18.8 ± 2.82 | — |
| JB + JA | 0.25 + 0.5 | 46.6 ± 0.81 | 0.78 |
| JB + JC | 0.25 + 0.5 | 40.2 ± 0.33 | 0.69 |
| JB + PC | 0.25 + 0.5 | 30.2 ± 4.37 | 0.82 |
| JB + JA + JC | 0.25 + 0.5 + 0.5 | 39.7 ± 6.28 | 0.88 |
| JB + JA + JC + PC | 0.25 + 0.5 + 0.5 + 0.5 | 43.9 ± 6.69 | 0.88 |
| JB + JA | 0.5 + 0.5 | 90.1 ± 3.93 | 0.49 |
| JB + JC | 0.5 + 0.5 | 86.2 ± 0.65 | 0.42 |
| JB + PC | 0.5 + 0.5 | 79.6 ± 1.80 | 0.45 |
| JB + JA + JC + PC | 0.5 + 0.5 + 0.5 + 0.5 | 88.7 ± 4.45 | 0.53 |
| Dexamethasone (positive control) | 0.5 | 118.7 ± 0.21 | — |
| Montelukast (positive control) | 0.5 | 40.2 ± 2.64 | — |

TABLE 6

| Test group | Concentration (μM) | Inhibition of splenocyte proliferation (%, n = 3, Mean ± SD) | CI value |
|---|---|---|---|
| Justicidin A (JA) | 1 | 43.4 ± 1.63 | — |
|  | 5 | 99.0 ± 2.35 | — |
| Justicidin B (JB) | 0.25 | 72.5 ± 2.66 | — |
|  | 0.5 | 90.8 ± 0.94 | — |
| Justicidin C (JC) | 1 | 6.7 ± 15.08 | — |
|  | 5 | 31.7 ± 12.81 | — |
| phyllamyricin C (PC) | 1 | 19.0 ± 18.44 | — |
|  | 5 | 25.0 ± 11.37 | — |
| JA + JB | 1 + 0.1 | 94.4 ± 0.94 | 0.40 |
|  | 1 + 0.2 | 94.8 ± 2.35 | 0.57 |
| JA + JC | 1 + 0.1 | 83.5 ± 1.90 | 0.26 |
|  | 1 + 0.2 | 85.9 ± 3.19 | 0.26 |
| JA + PC | 1 + 0.1 | 84.8 ± 2.73 | 0.25 |
|  | 1 + 0.2 | 86.0 ± 2.59 | 0.25 |
| JB + JC | 0.2 + 0.02 | 84.4 ± 1.40 | 0.49 |
|  | 0.2 + 0.04 | 80.5 ± 6.38 | 0.56 |
| JB + PC | 0.2 + 0.02 | 82.5 ± 0.84 | 0.52 |
|  | 0.2 + 0.04 | 82.0 ± 4.45 | 0.53 |
| 100% ethanol extract of *Justicia procumbens* L. | 2 μg/ml | 97.0 ± 0.91 | — |
| Dexamethasone (positive control) | 0.2 | 94.1 ± 1.80 | — |

As can be seen in Table 4 above, the inhibition of splenocyte proliferation almost never appeared in the case of the water extract of *Justicia procumbens* L., and the degree of inhibition increased as the concentration (%) of ethanol used for extraction increased. In addition, it was shown that treatment with the isopropanol extract and methanol extract of *Justicia procumbens* L. inhibited the proliferation of splenocytes by 43% and 36%, respectively.

Meanwhile, as shown in Tables 5 and 6 above, each of justicidin A, justicidin B, justicidin C and phyllamyricin C exhibited the effect of inhibiting splenocyte proliferation, even when it was used alone. In particular, justicidin A and justicidin B showed high inhibitory activities.

In addition, when treatment with justicidin A or justicidin B in combination with other three active substances exhibited higher inhibitory effects than treatment with justicidin A or justicidin B alone, and particularly, showed a CI value of less than 1, suggesting that administration of justicidin A or justicidin B in combination with other active substances shows synergistic effects.

TABLE 7

| Test group | Concentration (μM) | Inhibition of IL4 secretion (%, n = 2, Mean ± SD) | CI value | Inhibition of IL5 secretion (%, n = 2, Mean ± SD) | CI value |
|---|---|---|---|---|---|
| Justicidin A (JA) | 1 | -10.6 ± 0.08 | — | 25.4 ± 0.01 | — |
|  | 5 | 54.7 ± 0.02 | — | 56.7 ± 0.00 | — |
| Justicidin B (JB) | 0.5 | 35.9 ± 0.01 | — | 55.8 ± 0.01 | — |
|  | 1 | 78.2 ± 0.01 | — | 84.4 ± 0.00 | — |
| Justicidin C (JC) | 1 | -14.1 ± 0.05 | — | 39.8 ± 0.03 | — |
|  | 5 | 26.1 ± 0.04 | — | 36.4 ± 0.02 | — |
| Phyllamyricin C (PC) | 1 | 9.8 ± 0.05 | — | 22.9 ± 0.01 | — |
|  | 5 | 14.4 ± 0.01 | — | 67.9 ± 0.01 | — |
| JB + JA | 0.5 + 0.5 | 60.2 ± 0.01 | 0.73 | 72.4 ± 0.01 | 0.70 |
| JB + JC | 0.5 + 0.5 | 51.2 ± 0.01 | 0.80 | 70.0 ± 0.01 | 0.65 |
| JB + PC | 0.5 + 0.5 | 39.0 ± 0.03 | 0.94 | 71.5 ± 0.00 | 0.74 |
| JB + JA + JC + PC | 0.5 + 0.5 + 0.5 + 0.5 | 66.4 ± 0.01 | 0.73 | 84.0 ± 0.01 | 0.63 |

TABLE 7-continued

| Test group | Concentration (μM) | Inhibition of IL4 secretion (%, n = 2, Mean ± SD) | CI value | Inhibition of IL5 secretion (%, n = 2, Mean ± SD) | CI value |
|---|---|---|---|---|---|
| 100% ethanol extract of *Justicia procumbens* L. | 4 μg/ml | 80.7 ± 0.01 | — | 89.2 ± 0.00 | — |
| Dexamethasone (positive control) | 0.5 | 100.0 ± 0.00 | — | 103.3 ± 0.00 | — |
| Montelukast (positive control) | 10 | −42.6 ± 0.08 | — | 70.2 ± 0.01 | — |

TABLE 8

| Test group | Concentration (mM) | Inhibition of IL4 secretion (%, n = 2, Mean ± SD) | CI value | Inhibition of IL5 secretion (%, n = 2, Mean ± SD) | CI value |
|---|---|---|---|---|---|
| Justicidin A (JA) | 1 | 71.6 ± 0.02 | | 11.7 ± 0.27 | |
| | 5 | 86.4 ± 0.04 | | 25.7 ± 0.08 | |
| Justicidin B (JB) | 0.25 | 81.6 ± 0.02 | | 41.9 ± 0.04 | |
| | 0.5 | 87.6 ± 0.02 | | 66.8 ± 0.10 | |
| Justicidin C (JC) | 1 | 25.3 ± 0.15 | | 16.9 ± 0.06 | |
| | 5 | 51.7 ± 0.02 | | 26.2 ± 0.00 | |
| Phyllamyricin C (PC) | 1 | 11.8 ± 0.01 | | 0.5 ± 0.05 | |
| | 5 | 51.5 ± 0.11 | | 31.6 ± 0.08 | |
| JA + JB | 1 + 0.1 | 94.4 ± 0.00 | 0.27 | 90.1 ± 0.01 | 0.18 |
| | 1 + 0.2 | 94.8 ± 0.00 | 0.39 | 90.5 ± 0.00 | 0.31 |
| JA + JC | 1 + 0.1 | 91.7 ± 0.00 | 0.16 | 86.2 ± 0.01 | 0.05 |
| | 1 + 0.2 | 91.7 ± 0.00 | 0.17 | 87.2 ± 0.00 | 0.05 |
| JA + PC | 1 + 0.1 | 91.0 ± 0.00 | 0.17 | 85.8 ± 0.02 | 0.05 |
| | 1 + 0.2 | 92.0 ± 0.00 | 0.18 | 87.4 ± 0.03 | 0.06 |
| JB + JC | 0.2 + 0.02 | 92.2 ± 0.00 | 0.29 | 86.0 ± 0.01 | 0.29 |
| | 0.2 + 0.04 | 92.3 ± 0.00 | 0.29 | 82.5 ± 0.00 | 0.31 |
| JB + PC | 0.2 + 0.02 | 92.1 ± 0.00 | 0.29 | 85.3 ± 0.02 | 0.29 |
| | 0.2 + 0.04 | 90.5 ± 0.00 | 0.33 | 84.3 ± 0.00 | 0.30 |
| 100% ethanol extract of *Justicia procumbens* L. | 2 μg/ml | 95.4 ± 0.00 | | 91.5 ± 0.01' | |
| Dexamethasone (positive control) | 0.2 | 97.8 ± 0.00 | | 98.9 ± 0.01 | |

As shown in Tables 7 and 8 above, each of justicidin A, justicidin B, justicidin C and phyllamyricin C inhibited the secretion of IL4 and IL5, even when it was used alone. In addition, when treatment with justicidin A or justicidin B in combination with other active substances exhibited higher inhibitory effects than treatment with justicidin A or justicidin B alone, and particularly, showed a CI value of less than 1, suggesting that administration of justicidin A or justicidin B in combination with other active substances shows synergistic effects. Montelukast used as a positive control did not show the effect of inhibiting IL4 secretion, and showed only the effect of inhibiting IL5 secretion.

Example 3: Test for Evaluation of Expectorant Activity

In order to evaluate the expectorant activities of the water and ethanol extracts of *Justicia procumbens* L., prepared in Preparation Examples 1-1 to 1-2, a test for evaluation of expectorant activity was performed using male ICR mice (weighed 30 to 33 g; Orientbio). Specifically, the extracts and the comparative drug ambroxol (200 mg/kg, Boehringer Ingelheim) were administered orally to the respective groups of mice that fasted the previous day. After 30 minutes, 5% phenol red was injected intraperitoneally to the mice, and after 30 minutes, the abdominal aorta was cut to exsanguinate the animal, and the entire trachea was dissected. The isolated trachea was freeze-stored in 1 ml of physiological saline for 24 hours. Next, the trachea was sonicated, and 1N NaOH was added to the supernatant (0.1 ml of 1N NaOH per ml of the supernatant). Then, the absorbance at 546 nm was measured and the expectorant activity was measured with the concentration of phenol red. For statistical processing, calculation was performed using Equation 4 below, and the results are shown in Table 7 below.

Expectoration(%)=100−{(average absorbance value of test group−average absorbance value of normal group)/(average absorbance value of normal group)}×100 [Equation 4]

TABLE 9

| Test group | Drug concentration (mg/kg) | Expectoration (%, n = 4, Mean ± SE) |
|---|---|---|
| Normal group | | 0 ± 6.79 |
| Water extract | 200 | −31.8 ± 13.38 |
| 30% ethanol extract | 200 | 27.1 ± 23.31 |
| 50% ethanol extract | 200 | 58.0 ± 11.39 |
| 70% ethanol extract | 200 | 57.3 ± 15.26 |
| 100% ethanol extract | 200 | 41.2 ± 7.55 |
| Ambroxol (positive control) | 200 | 11.4 ± 12.89 |

As can be seen in Table 9 above, the water extract of *Justicia procumbens* L. had no expectorant activity, whereas the 30% to 100% ethanol extracts of *Justicia procumbens* L. had better expectorant activities than ambroxol used as the positive control.

Example 4: Test for Evaluation of Airway Hypersensitivity

In order to examine the effect of the ethanol extract of *Justicia procumbens* L. of Preparation Example 1-2 on the lung function, airway narrowing was induced by methacholine, and airway hypersensitivity was measured using whole-body plethysmography (DSI WBP System; DSIs Buxco Inc., USA). To this end, 6-week-old female Blab/c mice as experimental animals were purchased and randomly divided into a normal group, an induced group (negative control group) and a test group. The animals were acclimated for 1 week, and on 0 and 14 days after 1 week of acclimation, the induced group and the test group were systematically sensitized by intraperitoneally administering 0.1% ovalbumin (OVA: 1 mg/mL, Al(OH)$_3$: 20 mg/mL) in an amount of 100 μl/mouse. From one week after the final systematic sensitization (21 days), 200 mg/kg of the 100% ethanol extract of *Justicia procumbens* L. was administered orally to each test group every day for 10 days. As a positive control, 3 mg/kg of dexamethasone was administered intraperitoneally. After one hour, 0.2% ovalbumin solution was sprayed and inhaled into the mice for 1 hour by use of a nebulizer (PARI Boy SX, Germany GmbH). After final sensitization (30 days), the test animals were stabilized in the respective chamber biases for 12 minutes, and then methacholine was inhaled for 1 minute, followed by recording for 3 minutes, thereby measuring the data of airway hypersensitivity. The concentration of methacholine increased from 0, to 12.5, 25 and 50 mg/kg, and airway hypersensitivity was evaluated in terms of PenH value. The PenH value was calculated using Equation 5 below.

$$PenH = Pause \times \frac{PEF}{PIF} \quad Pause = \frac{Te - Tr}{Tr}$$ [Equation 5]

PIF: peak inspiratory flow;
PEF: peak expiratory flow;
Te: expiratory time;
Tr: relaxation time.

As shown in FIG. 4, 100% ethanol extract of *Justicia procumbens* L. inhibited airway hyperresistance as much as did dexamethasone used as the positive control.

Example 5: Evaluation of Airway Constriction Inhibition by Tissue Staining of OVA-Induced Balb/c Mice 5-week-old female Balb/c mice were purchased and acclimated for 1 week. On 0 and 14 days after 1 week of acclimation, the mice were systematically sensitized by intraperitoneally administering 0.1% ovalbumin (OVA: 1 mg/mL, Al(OH)$_3$: 20 mg/mL) in an amount of 100 μl/mouse. From one week after the final systematic sensitization (21 days), 200 mg/kg of the 100% ethanol extract of *Justicia procumbens* L. was administered orally to the mice every day for 10 days. After one hour, 0.2% ovalbumin solution was sprayed and inhaled into the mice for 1 hour by use of a nebulizer (PARI Boy SX, Germany GmbH). 5 hours after final sensitization (30 days), the mice were biopsied, and the lung tissue was taken and fixed in 10% neutral formalin. Thereafter, the lung tissue was sectioned to produce slices, and H & E staining was performed to observe the tissue. For tissue observation, the tissue was imaged with a microscope (400×). The subepithelial smooth muscle thickness and epithelium thickness of the imaged tissue were measured using Image-pro Plus 6.0 program. The results are shown in Table 10 below and FIG. 5.

TABLE 10

| | Normal group Mean ± S.D. | Induced group (OVA) Mean ± S.D. | *Justicia procumbens* L. (OVA + JP) 200 mg/kg Mean ± S.D. |
|---|---|---|---|
| Subepithelial smooth muscle thickness (μm) | 5.62 ± 1.15 | 7.35 ± 1.10 | 4.77 ± 0.36# |
| Epithelium thickness (μm) | 15.57 ± 1.47 | 36.99 ± 6.31* | 24.48 ± 3.50*# |

*$p < 0.05$ vs. normal group,
$p < 0.05$ vs. induced group

As a result, as can be seen in Table 10 above and FIG. 5, when the 100% ethanol extract of *Justicia procumbens* L. was administered orally, the thicknesses of subepithelial smooth muscles and epithelium, involved in airway constriction in lung tissue, decreased.

Example 6: Evaluation of Asthma Inhibitory Effect of *Justicia procumbens* L. Extract in Neutrophilic Asthma Balb/c Mouse Models 5-week-old female Balb/c mice were purchased and acclimated for 1 week. On 0 and 7 days after 1 week of acclimation, each of the mice was systematically sensitized by intranasally administering 75 μg of ovalbumin and 10 μg of lipopolysaccharide (LPS). 20, 50 or 100 mg/kg of the *Justicia procumbens* L. prepared in Preparation Example 3 or a positive control (10 mg/kg of dexamethasone and 1 mg/kg of montelukast) was administered orally to the mice On days 14, 15, 21, 22, 28, 29, 35, 36 and 37. One hour after administration, 50 μg of ovalbumin was administered intranasally to the mice. 24 hours after final sensitization (day 37), lung lavage fluid was obtained through tracheostomy, and the lung tissue was isolated. The collected lung lavage fluid was centrifuged at 3000 rpm for minutes, and the supernatant was used to measure physiologically active substances (IL-4, IL-5, and IFN-γ), and the pellets were used to measure the number of inflammatory cells. The physiologically active substances (interleukin-4 (IL-4), interleukin-5 (IL-5), and interferon-gamma (IFN-γ)) in the isolated lung lavage fluid were measured using an enzyme-linked immunosorbent assay (ELISA, IL-4: Komabiotech #K0331144, IL-5: R&D system #M5000, IFN-γ: Komabiotech #K0331138) corresponding to each substance. In addition, the lung lavage fluid pellets were re-dissolved in 0.5 mL of phosphate buffered saline, and 0.1 mL of the solution was added to each well of a 96-well plate and centrifuged at 800 rpm for 5 minutes to attach the cells to the bottom (3 wells per sample). Then, each sample was stained with Diff Quik staining solution (Sysmex), and photographed with a microscope at 2-6 random sites. About 200 cells per sample were counted and the percentage (%) of inflammatory cells of each sample was calculated. The total number of inflammatory cells was measured with a microscope using a hematocytometer, and the number of eosinophils and the number of neutrophils were calculated using the percentage (%) of inflammatory cells of each sample. Staining of the lung tissue was performed in the same manner as described in Example 5 above. Statistical processing was performed using an SPSS program, and a Levene test was performed for a test for equal variance, and significance was tested by one-way analysis (ANOVA).

The results are shown in Table 11 below and FIG. 6.

TABLE 11

| Test group (n = 5, Mean ± S.E.) | Lung lavage fluid_total inflammatory cell number ($\times 10^5$) | Lung lavage fluid_eosinophil number ($\times 10^5$) | Lung lavage fluid_neutrophil number ($\times 10^5$) | Lung lavage fluid_IL-4 (pg/mL) | Lung lavage fluid_IL-5 (pg/mL) |
|---|---|---|---|---|---|
| Normal group | 0.7 ± 0.04 | 0.0 ± 0.00 | 0.0 ± 0.00 | 36.2 ± 4.74 | 15.5 ± 9.54 |
| Induced group | 6.3 ± 0.10** | 1.3 ± 0.21** | 2.3 ± 0.13** | 256.1 ± 95.3** | 480.3 ± 143.4** |
| 20 mg/kg *Justicia procumbens* L. extract | 5.1 ± 0.30## | 0.8 ± 0.06## | 1.9 ± 0.21 | 83.6 ± 1.92## | 147.7 ± 6.38## |
| 50 mg/kg *Justicia procumbens* L. extract | 4.0 ± 0.13## | 0.6 ± 0.06## | 1.4 ± 0.10## | 69.8 ± 3.88## | 99.0 ± 3.45##, $$ |
| 100 mg/kg *Justicia procumbens* L. extract | 3.6 ± 0.17## | 0.6 ± 0.06## | 1.6 ± 0.07## | 74.0 ± 21.77## | 87.9 ± 10.61##, $$ |
| 10 mg/kg montelukast (positive control) | 4.0 ± 0.25## | 0.7 ± 0.05## | 1.5 ± 0.07## | 96.9 ± 14.40## | 194.4 ± 23.1## |
| 1 mg/kg dexamethasone (positive control) | 1.3 ± 0.07## | 0.1 ± 0.01## | 0.2 ± 0.02## | 32.1 ± 9.51## | 53.0 ± 13.59##, $$ |

| Test group (n = 5, Mean ± S.E.) | Lung lavage fluid_IFN-γ (pg/mL) | Epithelium thickness (μm) | Subepithelial smooth muscle thickness (μm) |
|---|---|---|---|
| Normal group | 0.0 ± 0.00 | 3.5 ± 0.28 | 1.3 ± 0.15 |
| Induced group | 121.3 ± 57.57** | 30.3 ± 2.94** | 11.3 ± 0.73** |
| 20 mg/kg *Justicia procumbens* L. extract | 22.8 ± 0.26##, $$ | 22.3 ± 1.23# | 9.4 ± 0.57 |
| 50 mg/kg *Justicia procumbens* L. extract | 11.7 ± 1.02##, $$ | 20.1 ± 1.53##, $ | 8.7 ± 0.39#, $ |
| 100 mg/kg *Justicia procumbens* L. extract | 7.2 ± 0.28##, $$ | 19.7 ± 1.51##, $ | 8.4 ± 0.40##, $ |
| 10 mg/kg montelukast (positive control) | 32.2 ± 2.13## | 25.5 ± 1.64 | 10.7 ± 0.59 |
| 1 mg/kg dexamethasone (positive control) | 1.3 ± 0.61##, $$ | 5.0 ± 0.38##, $$ | 2.7 ± 0.35 |

\*\*$p < 0.01$ vs. normal group,
\#$p < 0.05$ vs. induced group,
\#\#$p < 0.01$ vs. induced group,
$$p < 0.05$ vs. montelukast,
$$$p < 0.01$ vs. montelukast.

As a result, as Table 11 above and FIG. 6, in the neutrophilic asthma mouse models, the *Justicia procumbens* L. extract showed the effect of reducing the allergic asthma markers (IL-4, IL-5, and eosinophilic cells) in a concentration-dependent manner, and also showed the effect of reducing the non-allergic asthma markers (IFN-γ and neutrophilic cells). In addition, it was observed that the epithelium thickness and the subepithelial smooth muscle thickness also decreased depending on the concentration of the *Justicia procumbens* L. extract. Among these markers, IL-5, IFN-γ, the epithelium thickness and the subepithelial smooth muscle thickness more statistically significantly decreased in the group treated with the *Justicia procumbens* L. extract than in the group treated with the positive control montelukast.

Formulation Example 1: Preparation of Medicaments 1-1: Preparation of Powder

| Extract of a plant of the genus *Justicia* or a fraction thereof | 100 mg |
|---|---|
| Lactose | 100 mg |
| Talc | 10 mg |

The above components are mixed with one another and filled in an airtight container, thereby preparing powder.

1-2: Preparation of Tablet

| Extract of a plant of the genus *Justicia* or a fraction thereof | 100 mg |
|---|---|
| Corn starch | 100 mg |
| Lactose | 100 mg |
| Magnesium stearate | 2 mg |

The above components are mixed with one another, and compressed according to a conventional tablet preparation method, thereby preparing a tablet.

1-3: Preparation of Capsule

| Extract of a plant of the genus *Justicia* or a fraction thereof | 100 mg |
|---|---|
| Corn starch | 100 mg |
| Lactose | 100 mg |
| Magnesium stearate | 2 mg |

According to a conventional capsule preparation method, the above components are mixed with one another and filled in a gelatin capsule, thereby preparing a capsule.

1-4: Preparation of Injectable Solution

| Extract of a plant of the genus *Justicia* or a fraction thereof | 100 mg |
|---|---|
| Injectable sterile distilled water | q.s. |
| pH adjusting agent | q.s. |

According to a conventional method for preparation of an injectable solution, the above components are used per ampoule (2 ml), thereby preparing an injectable solution.

1-5: Preparation of Liquid Formulation

| Extract of a plant of the genus *Justicia* or a fraction thereof | 100 mg |
|---|---|
| Sugar | 20 g |
| Isomerized sugar | 20 g |
| Lemon fragrance | q.s. |

Purified water is added to a total volume of 1,000 ml. According to a conventional method for preparation of a liquid formulation, the above components are mixed with one another, and then filled in a brown bottle and sterilized, thereby preparing a liquid formulation.

Formulation Example 2: Preparation of Food

| Extract of a plant of the genus *Justicia* or a fraction thereof | 100 mg |
|---|---|
| Vitamin mixture | q.s. |
| Vitamin A acetate | 70 μg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 μg |
| Vitamin C | 10 mg |
| Biotin | 10 μg |
| Amide nicotinate | 1.7 mg |
| Folic acid | 50 μg |
| Calcium pantothenate | 0.5 mg |
| Mineral mixture | q.s. |
| Ferrous sulfate | 1.75 mg |
| Zinc oxide | 0.82 mg |
| Potassium phosphate monobasic | 15 mg |
| Potassium phosphate dibasic | 55 mg |
| Potassium citrate | 90 mg |
| Calcium carbonate | 100 mg |
| Magnesium chloride | 24.8 mg |

Although the contents of the vitamins and the mineral mixture are preferably those suitable for health functional foods, these contents may be optionally modified. According to a conventional method for preparation of health functional food, the above components are mixed with one another, and then prepared into a health functional food (e.g., nutritional candy) according to a conventional method.

Formulation Example 3: Preparation of Beverage

| Extract of a plant of the genus *Justicia* or a fraction thereof | 100 mg |
|---|---|
| Citric acid | 1000 mg |
| Oligosaccharide | 100 g |
| Plum concentrate | 2 g |
| Taurine | 1 g |

Purified water is added to a total volume of 900 ml. According to a conventional method for preparation of a health functional beverage, the above components are mixed with one another, and then stirred with heating at 85° C. for about 1 hour. Then, the resulting solution is filtered, and collected in a 2-liter sterilized container. Next, it is sealed, sterilized, cold-stored, and then used in the preparation of the health functional beverage composition of the present invention.

Although the above composition is a preferable example of components relatively suitable for favorite beverages, the contents thereof may be optionally modified according to regional and national preferences, including consumer characteristics, consumer nations, the intended use, etc.

The invention claimed is:

1. A method for preventing, treating or improving a respiratory disease, comprising administering to a subject in need thereof a composition comprising an extract of *Justicia procumbens* L,
wherein the extract is an alcohol extract or an organic solvent extract, and
wherein the composition is a pharmaceutical composition or a food composition.

2. The method of claim 1, wherein the *Justicia procumbens* L. is one or more selected from the group consisting of a whole plant, an aerial part, a root, a leaf, a flower and a seed.

3. The method of claim 1, wherein the extract is the alcohol extract, and the alcohol is a lower alcohol having 1 to 4 carbon atoms.

4. The method of claim 1, wherein the extract is the alcohol extract, and the alcohol extract is an ethanol extract.

5. The method of claim 1, wherein the extract is the alcohol extract, and the alcohol extract is a 30% ethanol extract, a 50% ethanol extract, a 70% ethanol extract or a 100% ethanol extract.

6. The method of claim 1, wherein the extract is the organic solvent extract, and the organic solvent is one or more selected from the group consisting of hexane, ethyl acetate, dichloromethane, ether, chloroform, and acetone.

7. The method of claim 1, wherein the respiratory disease is one or more selected from the group consisting of cold, pneumonia, bronchitis, asthma, chronic obstructive pulmonary disease, and rhinitis.

8. The method of claim 7, wherein the composition further comprises a functional health food.

9. The method of claim 1, wherein the extract comprises one or more selected from the group consisting of justicidin A, justicidin B, justicidin C, and phyllamyricin C.

10. The method of claim 9, wherein the composition further comprises a functional health food.

11. The method of claim 1, wherein the extract comprises: justicidin B; and one or more selected from the group consisting of justicidin A, justicidin C and phyllamyricin C.

12. The method of claim 11, wherein the composition further comprises a functional health food.

13. The method of claim 1, wherein the extract comprises: justicidin A; and one or more selected from the group consisting of justicidin B, justicidin C and phyllamyricin C.

14. The method of claim 13, wherein the composition further comprises a functional health food.

15. The method of claim 1, wherein the extract comprises justicidin B in an amount of 1 mg/g to 200 mg/g.

16. The method of claim 15, wherein the *Justicia procumbens* L. is one or more selected from the group consisting of a whole plant, an aerial part, a root, a leaf, a flower and a seed.

17. The method of claim 15, wherein the extract is the alcohol extract, and the alcohol is a lower alcohol having 1 to 4 carbon atoms.

18. The method of claim 15, wherein the extract is the alcohol extract, and the alcohol extract is an ethanol extract.

19. The method of claim 15, wherein the extract is the alcohol extract, and the alcohol extract is a 30% ethanol extract, a 50% ethanol extract, a 70% ethanol extract or a 100% ethanol extract.

20. The method of claim 15, wherein the extract is the organic solvent extract, and the organic solvent is one or more selected from the group consisting of hexane, ethyl acetate, dichloromethane, ether, chloroform, and acetone.

21. The method of claim 15, wherein the respiratory disease is one or more selected from the group consisting of cold, pneumonia, bronchitis, asthma, chronic obstructive pulmonary disease, and rhinitis.

22. The method of claim 15, wherein the food composition comprises a functional health food.

23. The method of claim 1, wherein the extract comprises justicidin A in an amount of 1 mg/g to 200 mg/g.

24. The method of claim 23, wherein the composition further comprises a functional health food.

25. The method of claim 1, wherein the extract comprises justicidin B in an amount of 1 mg/g to 200 mg/g and justicidin A in an amount of 1 mg/g to 200 mg/g.

26. The method of claim 25, wherein the composition further comprises a functional health food.

27. A method for preventing, improving, or treating a respiratory disease, comprising administering to a subject in need thereof a composition comprising justicidin A, justicidin B, or a mixture thereof, wherein the composition is a pharmaceutical composition or a food composition.

* * * * *